(12) United States Patent
Jang

(10) Patent No.: US 11,219,658 B2
(45) Date of Patent: Jan. 11, 2022

(54) COMPOSITION FOR PREVENTING OR TREATING DISEASES CAUSED BY CAFFEINE ABUSE INCLUDING EVODIA OFFICINALIS EXTRACT OR EVODIAMINE AS ACTIVE INGREDIENT

(71) Applicants: SG CORPORATION, Seoul (KR); Research & Business Foundation Sungkyunkwan University, Suwon-si (KR)

(72) Inventor: Choon Gon Jang, Suwon-si (KR)

(73) Assignees: SG CORPORATION, Seoul (KR); Research and Business Foundation Sungkyunkwan University, Suwon-si (KR)

(*) Notice: Subject to any disclaimer, the term of this patent is extended or adjusted under 35 U.S.C. 154(b) by 0 days.

(21) Appl. No.: 16/466,484

(22) PCT Filed: Dec. 1, 2017

(86) PCT No.: PCT/KR2017/014021
§ 371 (c)(1),
(2) Date: Jun. 4, 2019

(87) PCT Pub. No.: WO2018/105960
PCT Pub. Date: Jun. 14, 2018

(65) Prior Publication Data
US 2019/0314440 A1    Oct. 17, 2019

(30) Foreign Application Priority Data

Dec. 6, 2016 (KR) .................. 10-2016-0165353

(51) Int. Cl.
*A61K 36/00* (2006.01)
*A61K 36/754* (2006.01)
*A61P 25/30* (2006.01)
*A61K 31/4375* (2006.01)

(52) U.S. Cl.
CPC ........ *A61K 36/754* (2013.01); *A61K 31/4375* (2013.01); *A61P 25/30* (2018.01)

(58) Field of Classification Search
CPC ..................................... A61K 36/00
See application file for complete search history.

(56) References Cited

U.S. PATENT DOCUMENTS

2011/0275807 A1*  11/2011  Zhang .................. A61K 31/519
                                                                  544/245
2012/0322813 A1    12/2012  Linnet et al.

FOREIGN PATENT DOCUMENTS

| CN | 101019992 A |   | 8/2007 |            |
|----|-------------|---|--------|------------|
| CN | 103340872 A | * | 10/2013 |           |
| CN | 104367972 A | * | 2/2015 | ........... A61K 36/754 |
| CN | 104367972 A |   | 2/2015 |            |
| CN | 105639363 A | * | 6/2016 |            |
| JP | 04305527 A  | * | 10/1992 |           |
| KR | 10-1988-0001296 A |   | 4/1988 |      |
| KR | 20030070232 A | * | 8/2003 |           |
| KR | 10-2014-0086213 A |   | 7/2014 |      |
| KR | 10-2016-0085581 A |   | 7/2016 |      |

OTHER PUBLICATIONS

Wu, Effects of evodiamine on gastrointestinal motility in male rats. European journal of pharmacology, (Dec. 20, 2002) vol. 457, No. 2-3, pp. 169-176 (Year: 2002).*
Definition of hangover from Wikipedia, accessed on Aug. 30, 2020, pp. 1-14 (Year: 2020).*
Wu et al, Effects of evodiamine on gastrointestinal motility in male rats: European journal of pharmacology, (Dec. 20, 2002) vol. 457, No. 2-3, pp. 169-176 (Year: 2002).*
International Search Report dated Mar. 5, 2018 in counterpart International Application No. PCT/KR2017/014021 (3 pages in English, 3 pages in Korean).
Tsai et al., "Effects of Evodia rutaecarpa and Rutaecarpine on the Pharmacokinetics of Caffeine in Rats", Planta Med, 2005, vol. 71(7), (pp. 640-645).
Noh et al., "Effects of Rutaecarpine on the Metabolism and Urinary Excretion of Caffeine in Rats", Archives of Pharmacal Research, 2011, vol. 34(1), (pp. 119-125).
Seo et al., "Effects of Rutaecarpine on the Pharmacokinetics of Caffeine and Its Three Metabolites in Rats", Biomolecules & Therapeutics, 2011, vol. 19(2), (pp. 243-247).
Chinese Office Action dated Jul. 22, 2021 in counterpart Chinese Patent Application No. 201780075654.2 (6 pages in Chinese).

* cited by examiner

*Primary Examiner* — Qiuwen Mi
(74) *Attorney, Agent, or Firm* — NSIP Law

(57) ABSTRACT

The present invention relates to a composition which is for preventing or treating caffeine abuse and includes evodiamine or *Evodia officinalis* extract. More specifically, the present invention relates to a pharmaceutical composition which has an effect of preventing or alleviating somnipathy and central nervous system excitation caused by caffeine. In addition, the present invention relates to a caffeine abuse treatment method and a health functional food composition including *Evodia officinalis* extract or evodiamine.

2 Claims, 5 Drawing Sheets

COMPOSITION FOR PREVENTING OR TREATING DISEASES CAUSED BY CAFFEINE ABUSE INCLUDING EVODIA OFFICINALIS EXTRACT OR EVODIAMINE AS ACTIVE INGREDIENT

CROSS-REFERENCE TO RELATED APPLICATIONS

This application is a national stage application under 35 U.S.C. § 371 of International Patent Application Serial No. PCT/KR2017/014021 filed on Dec. 1, 2017, which claims the benefit of priority to Korean Patent Application No. 10-2016-0165353 filed on Dec. 6, 2016, in the Korean Intellectual Property Office, the entire disclosures of which are incorporated herein by reference for all purposes.

TECHNICAL FIELD

The present invention relates to a composition including an *Evodia officinalis* extract or evodiamine for preventing or treating a disease caused by caffeine abuse, and more particularly, to a pharmaceutical composition effective in preventing or improving somnipathy and central nervous system stimulation, which are induced by caffeine. In addition, the present invention relates to a method and health functional food composition including evodiamine for treating a disease caused by caffeine abuse.

BACKGROUND ART

According to westernized eating habits and a busy lifestyle, modern people are consuming various types of beverages, and in the selection criteria of food, the westernization tendency has increased, and thus, particularly, the consumption of caffeine-rich favorite beverages is increasing day by day. As a result, various caffeine-containing processed foods are being developed, and due to the increase in the use of coffee shops or fast-food restaurants, the consumption of caffeinated foods is increasing for all ages. A study on the coffee consumption market has reported that one person consumes 0.8 cup of coffee daily, and the number of yearly consumed cups is 300 cups. In addition, many teens drink coffee containing caffeine, and considering beverages and chocolates containing excessive caffeine, there may be a risk of overdosing of caffeine. Caffeine, a type of favorite food, has been widely used in society, and is contained in cola, chocolate, etc., which are popular with children or teens, as well as coffee or tea, and also in non-prescription medicines such as a headache medicine, a cold medicine, a diuretic and an anorectic agent as well as food and beverages.

Caffeine is widely contained in coffee, tea, beverages, medicines, etc., and its main component is 1,3,7-trimethylxanthine, which is a bitter nitrogen-containing alkaloid compound, derived from purine and uric acid. Caffeine is an odorless white needle-like crystal that is sublimated at 176 well dissolved in hot water and has a distinctive bitter taste. In addition, caffeine is known to be present in leaves and fruits of about 60 types of plants, and is mainly extracted from seeds of coffee trees (*Coffee arabica*). In addition, caffeine is also extracted from leaves of tea trees (*Camellia sinensis* (L) O. Kuntze), fruits of cacao trees (*Theobroma cacao*), fruits of kola trees (*Cola acuminata*), and leaves of mate trees (*Ilex paraguayensis*).

Caffeine, a type of central nervous system stimulant for stimulating the central nervous system and the sympathetic nervous system, affects organs of the body, for example, the integumentary system, bone marrow, and the spinal cord. Experimental studies on the physical effects of caffeine have revealed the effects of absorption in the body, and it is known that a blood concentration of a stress hormone such as adrenaline, noradrenaline or cortisol is generally increased, thereby increasing blood pressure. Caffeine has an effect of stimulating the central nervous system and thus is widely used as a stimulant for overcoming drowsiness. As the sleeping disorder and the stimulating effect have been known to the public, highly caffeinated beverages have become popular and thus widely used. However, long-term intake has a serious effect on normal sleep and a stimulated state, and it has been reported that caffeine overdose can bring about risks of indigestion, palpitations, excitation, headaches, insomnia, hyperacidic gastritis, diuresis, mineral deficiency, etc.

Particularly, highly caffeinated beverages currently popular among teens are misunderstood as "drugs for studying for exams" and many teens are drinking these beverages in the test period. However, highly caffeinated beverages only have an effect of stimulating the central nervous system to temporarily shake off sleepiness, and there is no evidence that these beverages can help in improving grades. Like this, while there is a lack of good understanding about highly caffeinated beverages, in Korea, there are no special legal provisions for protecting teens and children from drinking of the highly caffeinated beverages, and there is a problem of no legal restrictions on the sale of highly caffeinated beverages based on their harmfulness. Moreover, to date, no specific preventive and therapeutic agents for improving caffeine abuse have been suggested yet.

Meanwhile, evodiamine is a type of indole alkaloid having a molecular formula of $C_{19}H_{17}N_3O$ and a molecular weight of 303.36 and is a compound contained in the fruits of plants in the family Rutaceae such as *Tetradium daniellii*. Evodiamine is biosynthesized from tryptophan and anthranyl acid, has a yellow plate-like crystal and is well dissolved in acetone. It has been reported that evodiamine is a natural substance isolated form a plant, which hardly has cytotoxicity in a living organism and can prevent skin aging (Korean Unexamined Patent Publication No. 10-2016-0085581) and treat inflammation induced by obesity (Korean Unexamined Patent Publication No. 10-2014-0086213).

It also has been reported that evodiamine increases body heat production, and is effective in inhibiting an appetite due to its effect on a catecholamine level, but the effect of evodiamine on a disease caused by caffeine abuse has not been elucidated.

Under this background, the inventors confirmed an effect of preventing or improving somnipathy and central nervous system stimulation due to caffeine induction in mice using evodiamine, and thus the present invention was completed.

DISCLOSURE

Technical Problem

The present invention is directed to providing a pharmaceutical composition including evodiamine or an *Evodia officinalis* extract as an active ingredient for preventing or treating a disease caused by caffeine abuse.

The present invention is also directed to providing a method for preventing or treating a disease caused by caffeine abuse, which includes administering the composition to a subject.

The present invention is also directed to providing a use of the composition for preventing or treating a disease caused by caffeine abuse.

The present invention is also directed to providing a health functional food composition including evodiamine or *Evodia officinalis* extract as an active ingredient for improving a disease caused by caffeine abuse.

However, technical problems to be solved by the present invention are not limited to the above-described problems, and other problems which are not described herein will be fully understood by those of ordinary skill in the art from the following descriptions.

Technical Solution

To attain the objects of the present invention, the present invention provides a pharmaceutical composition including evodiamine or *Evodia officinalis* extract as an active ingredient for preventing or treating a disease caused by caffeine abuse.

The present invention also provides a method for preventing or treating a disease caused by caffeine abuse, which includes administering the above composition to a subject.

The present invention also provides a use of the composition for preventing or treating a disease caused by caffeine abuse.

The present invention also provides a health functional food composition including evodiamine or an *Evodia officinalis* extract as an active ingredient to improve a disease caused by caffeine abuse.

Advantageous Effects

In the present invention, a composition including evodiamine, *Evodia officinalis* extract or fraction thereof as an active ingredient can be effective in inhibiting central nervous system stimulation and improving somnipathy, and thus can be applied to a pharmaceutical composition or health functional food composition for preventing, treating or improving a disease caused by caffeine abuse.

MODES OF THE INVENTION

Figure 1:
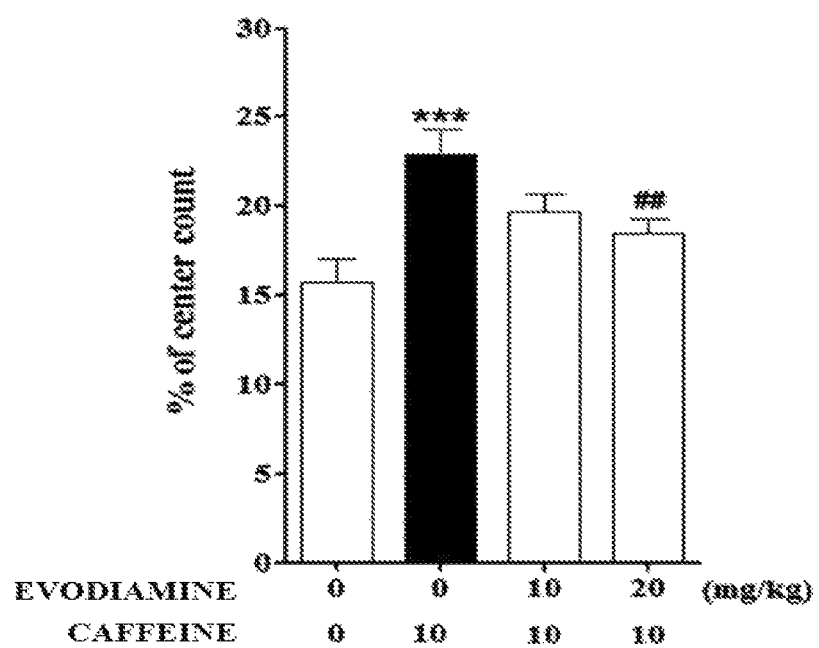
FIG. 1 is a graph showing an effect of evodiamine on the excitatory motor activity count % increased by caffeine abuse according to an exemplary embodiment of the present invention (***p<0.001 vs. solvent control, ##P<0.01 vs. caffeine control).

In one aspect, the present invention provides a pharmaceutical composition including evodiamine or *Evodia officinalis* extract as an active ingredient for preventing or treating a disease caused by caffeine abuse.

The term "evodiamine" used herein is a type of indole alkaloid having a molecular formula of $C_{19}H_{17}N_3O$ and a molecular weight of 303.36 and is a component contained in *Tetradium daniellii* and represented by Formula 1 below.

[Formula 1]

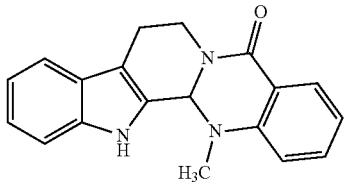

The evodiamine may be commercially available, or synthesized or extracted from *Evodia officinalis*, but the present invention is not limited thereto.

The term "caffeine abuse" used herein refers to abuse caused by caffeine, for example, abuse or dependency on caffeinated food such as coffee, highly caffeinated energy drinks, cola, green tea, black tea, or cocoa. A disease caused by the caffeine abuse may refer to one or more diseases selected from the group consisting of insomnia, diarrhea, excitement, headaches, a lack of concentration, nausea, vomiting, depression, anxiety, hand tremors, muscle pain and withdrawal symptoms, which are caused by various causes, regardless of caffeine dose and caffeine intake number.

In an exemplary embodiment of the present invention, as a result of administering the evodiamine of the present invention to a mouse model having motor activity increased by central nervous system stimulation due to caffeine abuse, an effect of inhibiting the central nervous system stimulation (FIGS. 1 to 3) was confirmed. This shows that the evodiamine can be effective in preventing, treating or improving a disease caused by caffeine abuse.

In the present invention, the pharmaceutical composition may include an *Evodia officinalis* extract or fraction thereof.

The term "*Evodia officinalis*" used herein is a deciduous tree belonging to the family Rutaceae, originating in China and residing in Gyeongju in Gyeongsangbuk-do, Korea. The *Evodia officinalis* may contain a volatile essential oil, and include the evodiamine as a main component. The *Evodia officinalis* may be commercially available, or cultivated or harvested.

The term "extract" used herein includes an extraction solution obtained by extraction of *Evodia officinalis*, a diluent or concentrate of the extraction solution, a dry product obtained by drying the extraction solution, partially or completely purified components of the extraction solution or a mixture thereof, an extract solution itself, and all available forms of extracts using the extraction solution. Specifically, the extract of the present invention may be used in the manner of being prepared in a powder form through extraction and freeze drying.

Regarding the *Evodia officinalis* extract of the present invention, a method of extracting the *Evodia officinalis* may be a method conventionally used in the art, but the present invention is not limited thereto. Non-limiting examples of extraction solvents may include water, alcohols, hexane and mixed solvents thereof, and when an alcohol is used as a solvent, as an example, a C1 to C4 alcohol may be used. As another example, the *Evodia officinalis* extract of the present invention may be specifically a hot water extract.

In addition, the extract may be subjected to extraction or fractionation, followed by vacuum filtration and concentration and/or freeze-drying for concentration or solvent removal, and the obtained *Evodia officinalis* extract may be stored in a quick-freeze refrigerator until use.

The term "fraction" used herein means a result obtained by performing fractionation to isolate a specific component or specific component group from a mixture containing various components.

In the present invention, a method of fractionating the fraction is not particularly limited, and may be a method conventionally used in the art. A non-limiting example of the fractionation method may be a method of obtaining fraction from extract obtained by extraction of *Evodia officinalis* by treating the extract with a predetermined solvent.

The type of a fractionation solvent used to obtain the fraction in the present invention is not particularly limited, and thus any solvent known in the art may be used. Non-limiting examples of the fractionation solvents may include polar solvents such as water, an alcohol, etc.; and non-polar solvents such as hexane, ethyl acetate, chloroform and dichloromethane. These solvents may be used alone or in combination of two or more thereof. When an alcohol among the fractionation solvents is used, specifically, a C1 to C4 alcohol may be used.

The composition may not include rutaecarpine.

Figure 4:
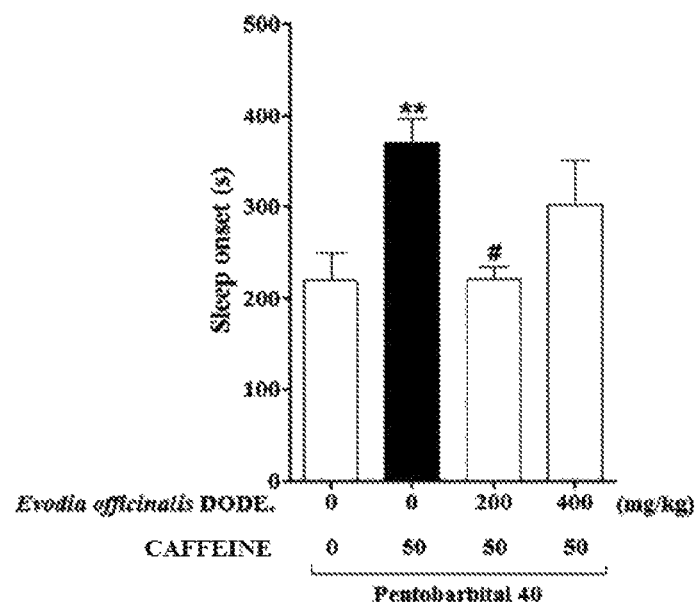
FIG. 4 is a graph showing an effect of *Evodia officinalis* extract on sleep onset in caffeine abuse somnipathy models according to an exemplary embodiment of the present invention (*Evodia officinalis* DODE, euodia extract; pentobarbital, 40Entobar®; **p<0.01 vs. solvent control, #p<0.05 vs. caffeine control, as referred to later).
Figure 5:
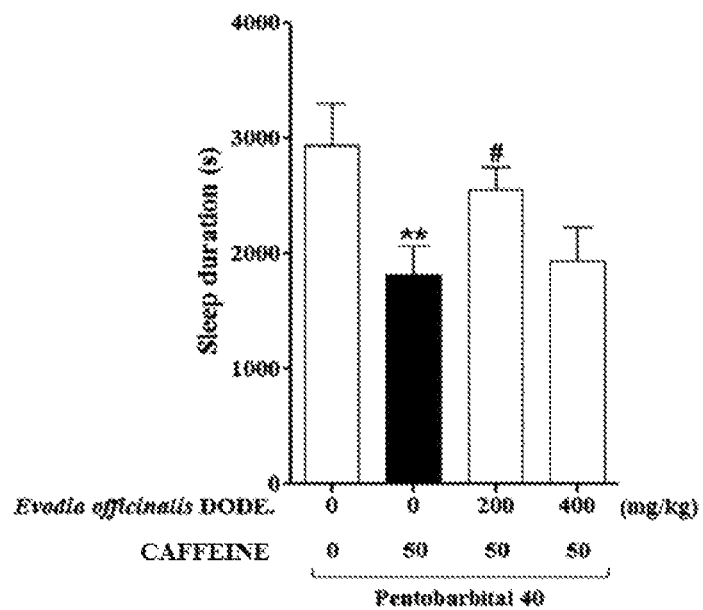
FIG. 5 is a graph showing an effect of *Evodia officinalis* extract on sleep duration in caffeine abuse somnipathy models.

In an exemplary embodiment of the present invention, as a result of administering the *Evodia officinalis* extract of the present invention to a mouse model having somnipathy caused by caffeine abuse, an effect of improving somnipathy caused by caffeine administration was confirmed (FIGS. 4 and 5). This suggests that the *Evodia officinalis* extract can be effective in preventing, treating or improving a disease caused by caffeine abuse.

The term "prevention" used herein refers to all actions of inhibiting or delaying a disease caused by caffeine abuse by administering the pharmaceutical composition including evodiamine or *Evodia officinalis* extract or fraction thereof according to the present invention.

The term "treatment" used herein refers to all actions involved in alleviating or beneficially changing a disease caused by caffeine abuse by administration of the pharmaceutical composition according to the present invention.

The pharmaceutical composition of the present invention may include 0.001 to 30 wt %, and specifically, 0.1 wt % to 20 wt % of evodiamine. *Evodia officinalis* extract or fraction thereof with respect to the total weight of the composition, but the present invention is not limited thereto.

The pharmaceutical composition for preventing or treating a disease caused by caffeine abuse according to the present invention may further contain a pharmaceutically acceptable carrier, and may be prepared with the carrier and applied to food, medicines, and drink additives.

The term "pharmaceutically acceptable" used herein means non-toxicity to cells or a human exposed to the composition, and the carrier may include a non-naturally occurring carrier. The composition including a pharmaceutically acceptable carrier may be prepared in various oral or parenteral forms. In preparation, the composition may be prepared using a diluent or excipient such as a filler, a thickening agent, a binder, a wetting agent, a dispersant or a surfactant, which is generally used. As the carrier, the excipient or the diluent, one or more selected from the group consisting of lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, physiological saline, methylhydroxybenzoate, propylhydroxybenzoate, talc, magnesium stearate, mineral oil, dextrin, calcium carbonate, propylene glycol and liquid paraffin may be used, but the present invention is not limited thereto, and all conventional carriers, excipients and diluents can be used. The components may be added independently or in combination with evodiamine, and *Evodia officinalis* extract or fraction thereof as an active ingredient.

A solid formulation for oral administration may be a tablet, pill, powder, granule or capsule, and such a solid formulation may be prepared by mixing at least one excipient, for example, starch, calcium carbonate, sucrose, lactose and gelatin one or more compounds. Also, in addition to the simple excipient, lubricants such as magnesium stearate and talc may also be used. As a liquid formulation for oral administration, a suspension, a liquid for internal use, an emulsion, or a syrup may be used, and a generally-used simple diluent such as water or liquid paraffin, as well as various types of excipients, for example, a wetting agent, a sweetener, a fragrance and a preservative may be included. A formulation for parenteral administration includes a sterilized aqueous solution, a non-aqueous solvent, a suspension, an emulsion, a lyophilized preparation and a suppository. As the non-aqueous solvent or suspension, propylene glycol, polyethylene glycol, a vegetable oil such as olive oil or an injectable ester such as ethyl oleate may be used. As a suppository base, witepsol, macrogol, Tween(tween) 61, cacao butter, laurin, or glycerogelatin may be used.

In addition, the pharmaceutical composition of the present invention may be prepared in any one form selected from the group consisting from a tablet, a pill, a powder, a granule, a capsule, a suspension, a liquid for internal use, an emulsion, a syrup, a sterilized aqueous solution, a non-aqueous solvent, a lyophilized preparation and a suppository.

The pharmaceutical composition of the present invention may be administered at a pharmaceutically effective amount. There is no particular limitation to a dose, which may be changed according to absorption in the body, a body weight, a patient's age, sex or health condition, diet, an administration time, an administration method, an excretion rate and the severity of a disease. The pharmaceutical composition of the present invention may be prepared in consideration of an effective amount range, and the unit-administration-type preparation prepared as described above may be administered using a specialized dosage regimen or at regular intervals several times according to the judgment or requirement of an expert inspecting or observing the administration of a drug as needed or the needs of an individual. Specifically, the pharmaceutical composition of the present invention may be administered daily at 0.1 to 50 mg/kg, and more specifically, 10 to 30 mg/kg, based on the amount of evodiamine, and the administration may be performed once a day or divided into several times. In addition, the pharmaceutical composition of the present invention is specifically administered daily at 0.1 to 500 mg/kg, more specifically, 1 to 400 mg/kg, still more specifically, 50 to 350 mg/kg, and even more specifically, 100 to 300 mg/kg, based on the *Evodia officinalis* extract or fraction thereof, and the administration may be performed once a day or divided into several times.

In another aspect, the present invention may provide a method of preventing or treating a disease caused by caffeine abuse using a pharmaceutical composition including evodiamine, and *Evodia officinalis* extract or fraction thereof as an active ingredient, the method including administering the pharmaceutical composition to a subject.

Here, the definitions of evodiamine, *Evodia officinalis*, an extract, fraction thereof, and prevention and treatment are the same as described above.

The term "administration" used herein means the introduction of a predetermined material to a subject by a suitable method, and an administration route of the composition may be any common route capable of reaching a desired tissue. The composition may be administered intraperitoneally, intravenously, intramuscularly, subcutaneously, intradermally, orally, locally, intranasally, intrapulmonarily, or intrarectally, but the present invention is not limited thereto.

The term "subject" used herein means all animals including humans in which a disease caused by caffeine abuse has occurred or will occur. As a specific example, the subject may include mammals including a human. In the present invention, a caffeine-administered subject may be included, or a subject into which evodiamine, an *Evodia officinalis* extract or fraction thereof is administered may be included.

In still another aspect, the present invention provides a health functional food composition including evodiamine, an *Evodia officinalis* extract or fraction thereof for improving a disease caused by caffeine abuse.

Here, the definitions of evodiamine, *Evodia officinalis*, extract, fraction and prevention are the same as described above.

The term "improvement" used herein means all types of actions that at least reduce parameters related to a condition to be treated by administration of the composition including the *Evodia officinalis* extract or evodiamine of the present invention, for example, a degree of a symptom.

When the composition of the present invention is used as an additive for a health functional food, evodiamine, an *Evodia officinalis* extract or fraction thereof may be suitably added as is or used in combination with a different food or food component according to a conventional method. A mixing amount of the active component may be suitably determined according to a purpose of use (prevention, health or therapeutic treatment), and since the composition of the present invention may be eco-friendly and have no problem in terms of stability, there is no limitation to a mixing amount.

Since the health functional food composition of the present invention can be routinely ingested, and thus an effect of improving a disease caused by caffeine abuse can be expected, it can be very useful for health improvement.

The term "health functional food" used herein is the same term as food for special health use (FoSHU), and means food having a high medical effect, which is processed to efficiently exhibit a bio-control function in addition to nutrient supply. Here, the term "function" means obtaining of an effect useful for control of a nutrient with respect to the structure and function of a human body or hygienic use such as a physiological action. The health functional food of the present invention can be prepared by a method conventionally used in the art, and may be prepared by adding a raw material and a component, which are conventionally added in the art during the preparation. In addition, a form of the health functional food may also be prepared without limitation as long as it is prepared in a form recognized as food. The composition for health functional food of the present invention may be prepared in various forms, and contains food as a raw material unlike general drugs, and thus has an advantage that no side effects can occur in long-term use of a drug and excellent portability. For this reason, the health functional food of the present invention can be taken as a supplement to enhance an effect of improving caffeine abuse.

The health functional food refers to food having an active health maintenance or improving effect, compared with common food, and health supplement food refers to food for health supplementation purposes. In this case, the terms of health functional food, health food, and health supplement food are used interchangeably.

Specifically, the health functional food is food prepared by adding the compound of the present invention to a food material such as beverages, teas, spices, gum or confectioneries, or prepared in the form of capsules, powder or a suspension. When ingested, the health functional food has a specific effect on health, but contains food as a raw material, unlike general drugs, and thus has an advantage that no side effects can occur due to long-term use of the drug.

The health functional food composition may further include a physiologically acceptable carrier, and the type of a carrier is not particularly limited, and thus any carrier used in the art may be used.

In addition, the health functional food composition may contain an additional component that can enhance smell, taste or visual appearance, which is generally used in a food composition. For example, the health functional food composition may contain vitamin A, C, D, E, B1, B2, B6 or B12, niacin, biotin, folate, or pantothenic acid. In addition, the health functional food composition may contain a mineral such as zinc (Zn), iron (Fe), calcium (Ca), chromium (Cr), magnesium (Mg), manganese (Mn) or copper (Cu); or an amino acid such as lysine, tryptophan, cysteine or valine.

In addition, the health functional food composition may contain food additives such as a preservative (potassium sorbate, sodium benzoate, salicylic acid, sodium dehydroacetate etc.), a sterilizer (bleaching powder, high-grade bleaching powder, sodium hypochlorite etc.), an antioxidant (butyl hydroxyanisole (BHA), butyl hydroxytoluene (BHT) etc.), a dye (tar pigment), a coloring agent (sodium nitride or sodium nitrate), a bleaching agent (sodium sulfate), a flavor enhancer (monosodium glutamate; MSG etc.), a sweetener (dulcin, cyclamate, saccharin, sodium etc.), a spice (vanillin, lactone etc.), a swelling agent (alum, potassium D-bitartrate etc.), a reinforcing agent, an emulsifier, a thickening agent (paste), a coating agent, a gum base agent, a foam inhibitor, a solvent and an improving agent. The additive may be selected according to the type of food and used at a suitable amount.

An example of the health functional food composition of the present invention may be a health beverage composition, and in this case, may contain additional components such as various flavoring agents or natural carbohydrates like a common beverage. The above-described natural carbohydrate may be a monosaccharide such as glucose or fructose; a disaccharide such as maltose or sucrose; a polysaccharide such as dextrin or cyclodextrin; sugar alcohol such as xylitol, sorbitol, or erythritol. The sweetening agent may be a natural sweetening agent such as a thaumatin or stevia extract; or a synthetic sweetening agent such as saccharin or aspartame. A ratio of the natural carbohydrate may generally be about 0.01 to 0.04 g, and specifically, about 0.02 to 0.03 g per 100 mL of the health beverage composition.

Other than these, the health beverage composition may contain various nutrients, vitamins, electrolytes, flavoring agents, coloring agents, pectic acid, salts of pectic acid, alginic acid, salts of alginic acid, organic acid, protective colloidal thickening agents, pH adjusters, stabilizers, preservatives, glycerin, alcohols, or carbonation agents. Other than theses, the health beverage composition may contain fruit or vegetable pulp for preparing a natural fruit juice, a fruit juice beverage or a vegetable beverage. These components may be used independently or in combination thereof. Ratios of the additives are not very significant, but are generally selected in the range of 0.01 to 20 parts by weight with respect to 100 parts by weight of the health beverage composition of the present invention.

Moreover, the present invention provides a use of a composition including evodiamine or an *Evodia officinalis* extract as an active ingredient for preventing or treating a disease caused by caffeine abuse.

Hereinafter, the present invention will be described in further detail with reference to examples. These examples are merely provided to illustrate the present invention, and it should not be construed that the scope of the present invention is limited by the following examples.

Example 1. Drugs and Reagents

Evodiamine, caffeine, dimethyl sulfoxide (DMSO) and Tween-20 were purchased from Sigma-Aldrich Chemistry Co., Ltd. Entobar® was purchased from Hanlim Pharm. Co., Ltd.

Example 2. Preparation of Experimental Animals 4-week-old ICR male mice (20 to 22 g) were provided from Koatech (Pyeongtaek, Korea), acclimated by breeding for 1 week or more in an animal breeding room in the School of Pharmacy at Sungkyunkwan University, and freely fed water and feed. The temperature (23±2° C.), humidity (55±10%) and a dark/light cycle (12 hrs) were automatically controlled.

Example 3. Preparation of *Evodia officinalis* Extract

*Evodia officinalis* originating in China was purchased from the Kyungdong Market (Seoul, Korea). 193 g of dry *Evodia officinalis* was completely dried, ground, boiled in water at 70 to 80° C., cooled to 40° C., filtered through filter paper (Whatman, USA), and vacuum-concentrated using a rotary evaporator (EYELA, N-1000, Japan). The resulting product was freeze-dried, thereby obtaining 31 g of *Evodia officinalis* crude extract.

Experimental Example 1. Effect of Evodiamine in Improving or Inhibiting Caffeine-Induced Central Nervous System Stimulation To measure an inhibitory effect of evodiamine on caffeine-induced central nervous system stimulation, the mice prepared in Example 2 were divided into four groups of 12 mice, and treated with evodiamine and caffeine in a different manner. The first group was a group treated with distilled water containing 10% DMSO (control), the second group was a group treated with 10% DMSO-containing distilled water and 10 mg/kg of caffeine, the third group was a group treated with 10 mg/kg of evodiamine and 10 mg/kg of caffeine, and the fourth group was a group treated with 20 mg/kg of evodiamine and 10 mg/kg of caffeine.

Evodiamine was dissolved in 10% DMSO-containing distilled water, and orally administered to mice at doses of 0, 10 and 20 mg/kg, and 30 minutes later, intraperitoneally injected with caffeine 10 mg/kg of caffeine. Then, after 30 minutes, the mice were put into a motor ability measurement box (diameter: 30×30×30 (cm)), and measured for a total of 60 minutes using a video measurement and analysis system (Neurovision, Busan, Korea), followed by conversion of the improvement or inhibition in an increased excitatory motor activity count (center count), excitatory motor activity time (center time) and total movement of excitatory motor activity (total movement) to percentage (%).

As shown in FIG. 1, as a result of comparing the motor activity counts of the groups, while the percentage of movement in the center of the motor ability measurement box in the first group (control) not treated with caffeine was 16%, the percentage of movement in the center of the motor ability measurement box in the second group treated with caffeine was 23%, demonstrating that the excitatory motor activity count (%) was significantly increased by caffeine. Therefore, it was confirmed that central nervous system stimulation was significantly induced by caffeine. Meanwhile, the percentages (%) of the excitatory motor count induced by caffeine in the third group treated with 10 mg/kg of evodiamine and the fourth group treated with 20 mg/kg of evodiamine were decreased to 20% and 19%, respectively. Accordingly, it was confirmed that the central nervous system stimulation caused by caffeine administration was significantly decreased by evodiamine.

Figure 2:
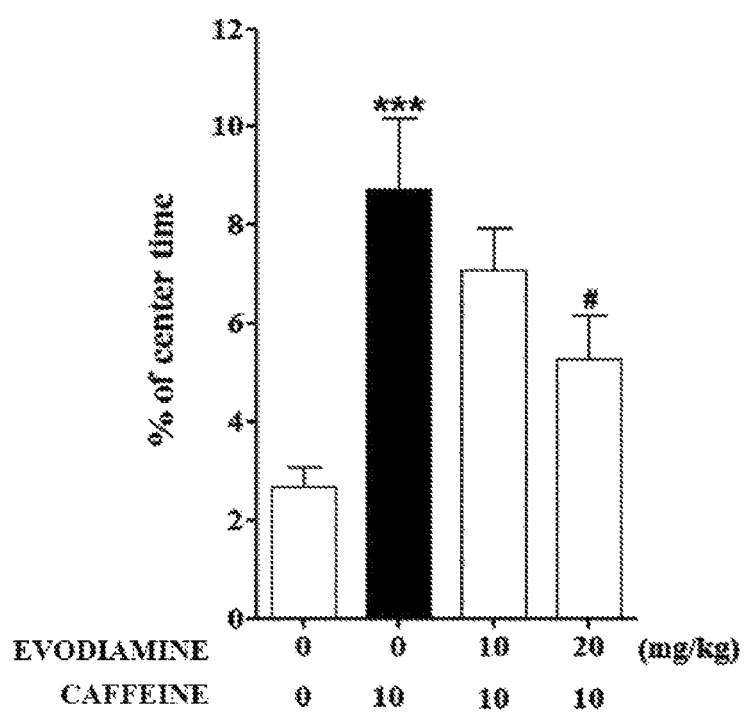
FIG. 2 is a graph showing an effect of evodiamine on the excitatory motor activity time % increased by caffeine abuse according to an exemplary embodiment of the present invention (***p<0.001 vs. solvent control, #P<0.05 vs. caffeine control).

In addition, as shown in FIG. 2, as a result of comparing motor activity time of the groups, while the percentage of maintenance in the center of the motor ability measurement box in the first group (control) not treated with caffeine was 3%, the percentage of maintenance in the center of the motor ability measurement box in the second group treated with caffeine was 9%, demonstrating that the excitatory motor activity time (%) was significantly increased by caffeine. Therefore, it was confirmed that the central nervous system stimulation was significantly induced by caffeine. Meanwhile, the percentages (%) of the motor activity time in the center of the box in the third group treated with 10 mg/kg of evodiamine and the fourth group treated with 20 mg/kg of evodiamine were 7% and 5%, respectively. Accordingly, it was confirmed that the central nervous system stimulation caused by caffeine administration was significantly decreased by evodiamine.

Figure 3:
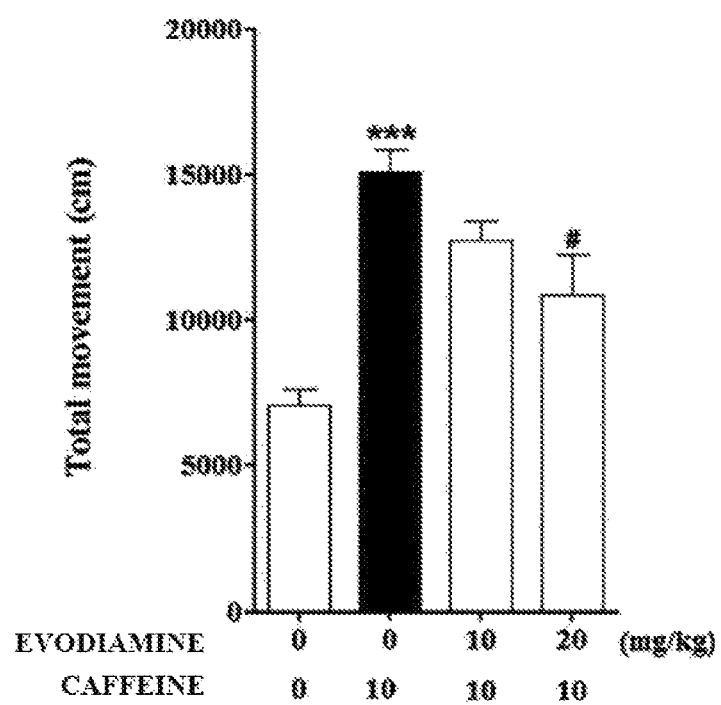
FIG. 3 is a graph showing an effect of evodiamine on the total movement of excitatory motor activity increased by caffeine abuse according to an exemplary embodiment of the present invention (***p<0.001 vs solvent control, #P<0.05 vs caffeine control).

A result of comparing the total movement of each group is shown in FIG. 3. While the total movement in the motor ability measurement box in the first group (control) not treated with caffeine was 7,107 cm, the total movement in the motor ability measurement box in the second group treated with caffeine was 15,078 cm, demonstrating that the total movement of a mouse was significantly increased by caffeine. Meanwhile, the total movement in the third group treated with 10 mg/kg of evodiamine and the fourth group treated with 20 mg/kg of evodiamine was decreased to 12,734 cm and 10,910 cm, respectively. Accordingly, it was confirmed that the central nervous system stimulation caused by caffeine administration was significantly decreased by evodiamine.

From the results of FIGS. 1 to 3, it was confirmed that evodiamine can be effective in improving or inhibiting caffeine-induced central nervous system stimulation.

Experimental Example 2. Effect of *Evodia officinalis* Extract in Improving Caffeine-Induced Somnipathy To prove an effect of *Evodia officinalis* extract in improving caffeine-induced somnipathy, the mice prepared in Example 2 were divided into four groups of 12 mice (the first to fourth groups), and treated with the *Evodia officinalis* extract prepared in Example 3, Entobar® and caffeine in a different manner. Specifically, the first group was a group treated with 10% DMSO-containing distilled water and 40 mg/kg of Entobar® as a control, the second group was a group treated with 10% DMSO-containing distilled water, 50 mg/kg of caffeine and 40 mg/kg of Entobar®, the third group was a group treated with 200 mg/kg of the *Evodia officinalis* extract, 50 mg/kg of caffeine and 40 mg/kg of Entobar®, and the fourth group was a group treated with 400 mg/kg of the *Evodia officinalis* extract, 50 mg/kg of caffeine and 40 mg/kg of Entobar®.

Regarding the administration method, the *Evodia officinalis* extract was dissolved in 10% DMSO-containing distilled water, orally administered to the mice at doses of 0, 200 and 400 mg/kg once a day for three days, and 30 minutes after the final administration. 50 mg/kg of caffeine was intraperitoneally injected into the mice. Thirty minutes after the caffeine injection, 40 mg/kg of Entobar® was intraperitoneally injected to induce sleep. Immediately after the Entobar® injection, the mice were put into each cage, and then sleep onset and sleep duration were measured.

As shown in FIG. 4, as a result of comparing the sleep onset in the groups, while the sleep onset in the first group not treated with caffeine (control) was 219 seconds, the sleep onset in the second group administered caffeine was 371 seconds. Accordingly, as the sleep onset was considerably increased due to caffeine, it was confirmed that somnipathy was significantly induced by caffeine abuse. Meanwhile, the sleep onsets were 222 seconds and 303 seconds in the third group treated with 200 mg/kg of the *Evodia officinalis* extract and the fourth group treated with 400 mg/kg of the *Evodia officinalis* extract, respectively, confirming that the sleep onset was accelerated. Accordingly, it was confirmed that the caffeine administration-induced somnipathy was significantly improved by the administration of the *Evodia officinalis* extract.

In addition, as shown in FIG. 5, as a result of comparing total sleep duration in each group, while the sleep duration in the first group not treated with caffeine (control) was 2,940 seconds, the sleep duration in the second group treated with caffeine was 1,812 seconds. Accordingly, as the sleep duration was significantly decreased by caffeine, it was confirmed that somnipathy was significantly induced by caffeine abuse. Meanwhile, the sleep durations were 2,558 seconds and 1.940 seconds in the third group treated with 200 mg/kg of the *Evodia officinalis* extract and the fourth group treated with 400 mg/kg of the *Evodia officinalis* extract, respectively, confirming that the total sleep duration was increased. Accordingly, it was confirmed that the caffeine administration-induced somnipathy was significantly improved by the administration of the *Evodia officinalis* extract.

From the result, it was confirmed that the *Evodia officinalis* extract can be effective in improving caffeine-induced somnipathy.

Experimental Example 3. Comparison of Somnipathy-Improving Effects of *Evodia officinalis* Extract and Evodiamine To compare caffeine-induced somnipathy-improving effects of the *Evodia officinalis* extract and evodiamine, the *Evodia officinalis* hot water extract prepared in Example 3, ethanol extract thereof and evodiamine were orally administered to the mice prepared in Example 2 once a day for 3 days. 30 minutes after the final administration, 50 mg/kg of caffeine was intraperitoneally injected into the mice. After thirty minutes. 40 mg/kg of Entobar® was intraperitoneally injected to induce sleep, followed by measuring sleep onset and total sleep duration.

The ethanol extract used was prepared by extracting a ground and dried product of 600 g of *Evodia officinalis* using 50% ethanol at room temperature for three times in the same manner as described in Example 3 (yield: 55.5 g).

As shown in Table 1, it can be confirmed that the sleep onset and the total sleep duration are significantly increased by administering the *Evodia officinalis* extract and evodiamine.

Meanwhile, when 200 mg/kg of the *Evodia officinalis* hot water extract or 10 mg/kg of evodiamine was administered, the sleep onset was exhibited at a similar level. Even though the dose was reduced to $1/20$, it was surprisingly shown that evodiamine exhibits a similar somnipathy-improving effect, compared to the *Evodia officinalis* hot water extract.

In addition, when 5 mg/kg of evodiamine was administered, the total sleep duration was increased to that of the normal group (vehicle) not treated with caffeine, but in the case of the *Evodia officinalis* extract, even though it was administered at a dose (200 mg/kg) 40-fold higher than that of evodiamine, the evodiamine effect was still superior to that of the *Evodia officinalis* extract.

Therefore, it was confirmed that evodiamine has an effect in improving caffeine-induced somnipathy even at a significantly lower dose than that of the *Evodia officinalis* extract.

Meanwhile, compared with the *Evodia officinalis* ethanol extract, the effect of the *Evodia officinalis* hot water extract in improving the sleep onset barrier was increased 11% or more, which was induced by caffeine, and particularly, the ethanol extract had no significant effect in improving the total sleep duration, but the hot water extract exhibited a significant improvement effect.

TABLE 1

| | Change in sleep onset (% of Control) | Change in total sleep duration (% of Control) |
|---|---|---|
| Vehicle control | 100 | 100 |
| Caffeine | 166.8 *** | 57.4 ** |
| Caffeine + DW 200 mg/kg | 101.0 # | 88.9 # |
| Caffeine + EtOH 200 mg/kg | 112.5 # | 69.7 |
| Caffeine + Evo 5 mg/kg | 138.7 | 100.5 # |
| Caffeine + Evo 10 mg/kg | 108.2 # | 94.0 |

(Vehicle control: 10% DMSO-containing distilled water, DW; Evodia officinalis hot water extract, EtOH; Evodia officinalis ethanol extract, Evo; evodiamine-administered group, * $P < 0.001$,  $P < 0.01$ vs. Vehicle group, # $P < 0.05$ vs. caffeine group)

Experimental Example 4: Statistical Treatment

All experimental results were analyzed using one way analysis of variance (ANOVA), and when the significance was verified, an LSD test was used to confirm significance at $p<0.05$.

From the above description, it will be understood by those of ordinary skill in the art to which the present invention pertains that the present invention can be embodied in different specific forms without changing the technical spirit or essential characteristics thereof. In this regard, it should be understood that the above-described embodiments are merely illustrative and not limitative in all aspects. The scope of the present invention is defined by the appended claims and encompasses all modifications and alterations derived from meanings, the scope and equivalents of the appended claims.

INDUSTRIAL APPLICABILITY

A composition including evodiamine, *Evodia officinalis* extract or fraction thereof as an active ingredient according to the present invention is effective in inhibiting central nervous system stimulation by caffeine abuse and improving somnipathy, and thus can be effectively used for preventing, treating or improving a disease caused by caffeine abuse, and improving somnipathy.

The invention claimed is:

1. A method of treating a disease, which comprises administering a composition consisting of an *Evodia rutaecarpa* extract as an active ingredient and a pharmaceutically acceptable carrier to a subject having caffeine dependence in need of a treatment, wherein the disease is selected from the group consisting of insomnia, hand tremors and muscle pain.

2. The method of claim 1, wherein the *Evodia rutaecarpa* extract is extracted using one or more types of solvents selected from water and alcohols having 1 to 4 carbon atoms.

* * * * *